(12) United States Patent
Santaniello et al.

(10) Patent No.: US 6,465,515 B2
(45) Date of Patent: Oct. 15, 2002

(54) SOLID COMPOSITIONS SUITABLE FOR ORAL ADMINISTRATION CONTAINING NON-HYDROSCOPIC SALTS OF L-CARNITINE AND ALKANOYL L-CARNITINES

(75) Inventors: Mosè Santaniello, Nettuno (IT); Nazareno Scafetta, Pavona di Albano (IT); Maria Ornella Tinti, Rome (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 0 days.

(21) Appl. No.: 09/740,786

(22) Filed: Dec. 21, 2000

(65) Prior Publication Data

US 2001/0009923 A1 Jul. 26, 2001

Related U.S. Application Data

(63) Continuation of application No. PCT/IT99/00202, filed on Jul. 2, 1999.

(30) Foreign Application Priority Data

Jul. 3, 1998 (IT) .................................. RM98A0445

(51) Int. Cl.$^7$ .................. A61K 31/22; C07C 69/52; C07C 63/34

(52) U.S. Cl. .................... 514/547; 514/533; 560/196; 562/467; 562/567

(58) Field of Search ................... 514/533, 547; 560/196; 562/467, 567

(56) References Cited

U.S. PATENT DOCUMENTS

| | | | |
|---|---|---|---|
| 4,602,039 A | 7/1986 | Cavazza | |
| 4,673,534 A | * 6/1987 | Gennari | .................. 260/501.12 |

FOREIGN PATENT DOCUMENTS

| | | | |
|---|---|---|---|
| DE | 38 41 664 A | | 10/1990 |
| EP | 0 167 115 A | | 1/1986 |
| EP | 0 434 088 A | | 6/1991 |
| GB | 2008578 | * | 2/1978 |

* cited by examiner

*Primary Examiner*—James O. Wilson
*Assistant Examiner*—Leigh C. Maier
(74) *Attorney, Agent, or Firm*—Nixon & Vanderhye P.C.

(57) ABSTRACT

Non-hygrocopic salts of L-carnitine and of the lower alkanoyl L-carnitines with pamoic acid are described, which are used to prepare solid compositions suitable for oral administration. Solid compositions containing such salts are also described.

9 Claims, No Drawings

SOLID COMPOSITIONS SUITABLE FOR ORAL ADMINISTRATION CONTAINING NON-HYDROSCOPIC SALTS OF L-CARNITINE AND ALKANOYL L-CARNITINES

This is a continuation of PCT application PCT/IT99/00202, filed Jul. 2, 1999, the entire content of which is hereby incorporated by reference in this application.

The invention described herein relates to non-hygroscopic salts of L-carnitine and lower alkanoyl L-carnitines which lend themselves favorably to the preparation of solid compositions suitable for oral administration. The invention also relates to the compositions thus obtained.

It is well known that L-carnitine and its derivatives lend themselves to various therapeutic uses. For example, carnitine is used in the cardiovascular field for the treatment of acute and chronic myocardial ischaemia, angina pectoris, heart failure and arrhythmias.

In the nephrological field, L-carnitine is administered to chronic uraemic patients undergoing regular haermodialytic treatment to combat muscular asthenia and the occurrence of muscle cramps.

Other therapeutic uses have to do with normalisation of the HDL:LDL-VLDL ratio and total parenteral nutrition.

It is also well known that the salts of carnitine and its alkanoyl derivatives present the same therapeutic or nutritional activities as the so-called "inner salts" and that they can therefore be used in their stead, provided the salts are "pharmacologically acceptable", i e. they do not present toxic side effects.

In practice, then, the choice between the "inner salt" or a true salt of L-carnitine or alkanoyl L-carnitine depends more on which compound is more easily and economically available and on The European Patent Application EP 0 167 115 describes a novel derivatives of L-carnitine or of acyl L-carnitines or esters thereof, obtained by salfication with suitable acids or acidic aminoacids, monosalifed with potassium ion, and pamoic acid belongs to the mentioned acids groups. U.S. Pat. No. 4,602,039 describes a novel L-carnitine or alkanoyl L-carnitine salts with a suitable acid, and among the listed acid pamoic acid is not mentioned. considerations of pharmaceutical technology rather than on considerations of therapeutic or nutritional activity.

It should therefore be clearly understood that, as far as the invention described herein is concerned, the usefulness of the above-mentioned salts does not consist in their different therapeutic or nutritional activity from those of known compounds but in their non-hygroscopicity vis-a-vis the corresponding internal salts.

Their non-hygroscopicity allows them to be easily processed, particularly with a view to the preparation of solid oral administration forms.

As is well known to experts in pharmaceutical technology, the processing of hygroscopic products entails the use of controlled-humidity chambers both for storage and for processing. Moreover, the finished product must be packaged in hermetically sealed blister packs to avoid the unwanted consequences of humidity.

All this entails greater costs both of storage of raw materials and of processing and packaging of the products.

Among the populations of the industrialised countries there is an increasingly widespread use of food supplements or "nutraceuticals" both by sportsmen (amateurs or professionals) and by people enjoying good health.

The former use L-carnitine or food supplements containing carnitine because it favours the oxidation of fatty acids and provides the skeletal muscles with a greater amount of energy, thus enhancing performance and giving rise to less build-up of lactic acid in the muscles.

People enjoying good health use these food supplements as health foods, i.e. for the purposes of preventing diseases related to disorders of lipid metabolism.

It has been estimated that the amount of L-carnitine and its derivatives sold for non-ethical purposes is twice that sold for ethical purposes.

The US market for food supplements or nutraceuticals amounts to approximately 250 billion dollars, while in Europe a market worth approximately 500 billion dollars has been estimated (Food Labeling News, 1994, "Nutraceuticals market said to be a vast one, March, Vol. 2, No 25; King Communications Group Inc., 1993. "Nutraceuticals" Foods. Drink in Global market, Food and Drink Daily, April, Vol. 3, No. 503).

A number of non-hygroscopic salts of L-carnitine are already known.

For example, European Patent 0 434 88, (Lonza), filed on Dec. 12, 1990, describes the use of a non-hygroscopic salt of L-carnitine with L-(+)-tartaric acid. (salt already described, moreover, by Müler and Strack in Hoppe-Seyler's Z. Physiol. Chem., 353, 618–622, April 1972) for the preparation of solid oral administrations forms.

These salts, however, present certain drawbacks, such as, for instance, the release of trimethylamine after prolonged storage, which gives rise to an unpleasant olfactory effect due to the characteristic fishy odour of this amine. Furthermore, L-(+)-tartaric acid is not capable of forming non-hygroscopic salts with the lower alkanoyl L-carnitines, such as, for instance, acetyl L-carnitine.

The purpose of the invention described herein is to provide new non-hygroscopic salts both of L-carnitine and the lower alkanoyl L-carnitines. These compounds are the salts with pamoic acid with the following general formula:

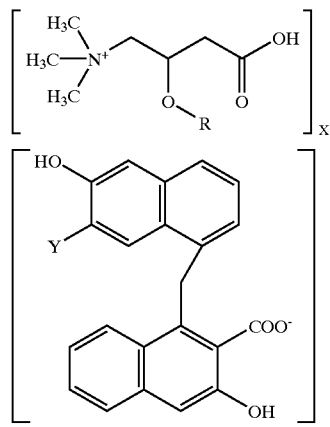

where:
R is hydrogen or a lower alkanoyl, linear or branched, with 2–6 carbon atoms;
if X=1, Y=COOH; and
if X=2, Y=COO—

Those salts are preferred in which R is selected from the group consisting of acetyl, propionyl, butyryl, valeryl and isovaleryl.

The salts of L-carnitine and the lower alkanoyl L-carnitines according to the invention are not hygroscopic and are extremely stable on storage.

The pamoates are pharmacologically acceptable salts approved by the Food and Drug Administration (FDA), as results, for example, from Int. J. Pharm., 33 (1986), 201–217.

Unlike the known salts of L-carnitine and alkanoyl L-carnitines, which are all hydrosoluble, the pamoates according to the invention are compounds endowed with poor hydrosolubility.

This property can be used to advantage to produce compositions with slow-release (or controlled release) of the active ingredient consisting in L-carnitine or one of its alkanoyl derivatives for the purposes of improving its absorption and prolonging the period of time during which blood levels of the compound are suitable for exerting the desired therapeutic or nutritional effect.

It is well known, in fact, that L-carnitine is a highly hydrosoluble compound and that it is rapidly excreted via the kidneys. Therefore, the administration of L-carnitine ensures adequate blood levels of the compound over too short a period for it to be able to perform for example, a protective function on the myocardium after myocardial ischaemia.

The subject matter of the invention described herein therefore also covers pharmaceutical, dietetic or nutritional compositions which produce slow, controlled release of L-carnitine or of its alkanoyl derivative.

If one desires to achieve high blood levels of L-carnitine or its alkanoyl derivative within a relatively short space of time and then maintain such optimal blood levels for a prolonged time period, according to the invention described herein one can use a composition consisting of a mixture of L-carnitine and/or alkanoyl L-carnitine in the form of a highly hydrosoluble salt, e.g. inner salt or hydrochloride, which makes all the L-carnitine or alkanoyl L-carnitine present in the composition immediately available, and one or more pamoates according to the invention, which, by slowly releasing the active ingredient, maintain substantially constant blood levels of this ingredient over a protracted period.

The invention described herein therefore also comprises a composition suitable for covering the daily requirement of L-carnitine and/or an alkanoyl L-carnitine, in which the alkanoyl has 2–6 carbon atoms, in an individual requiring such treatment, containing said L-carnitine and/or alkanoyl L-carnitine partly (a) in a free, immediately available form and partly (b) in a form ensuring its controlled release, characterised in that the ingredient (a) contains L-carnitine or alkanoyl L-carnitine in the form of inner salts or pharmacologically acceptable hydrosoluble salts; and ingredient (b) contains a salt of L-carnitine or alkanoyl L-carnitine with pamoic acid with general formula (I).

There now follow a number of examples, though not exclusively these, of the preparation of non-hygroscopic salts according to the invention.

EXAMPLE 1

Preparation of Propionyl L-carnitine Pamoate (ST 1324)

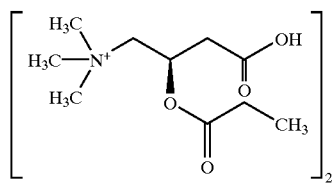

-continued

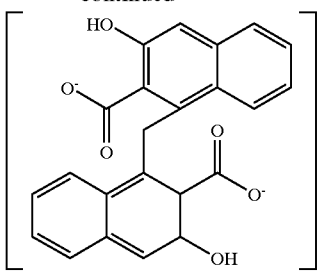

Propionyl L-carnitine chloride (5.6 g; 0.02 mol) was dissolved in the minimum amount of $H_2O$ and eluted on an IRA 492 Amberlite Resin column activated in the form of $HCO_3^-$.

Approximately 100 cc of eluate containing propionyl L-carnitine internal salt were percolated directly onto pamoic acid (3.88 g; 0.01 mol).

Acetone 100 ml was added to the mixture. The mixture was then stirred overnight until complete solubilisation was achieved.

The solution was vacuum-concentrated to dryness at 40° C. Isopropanol was added to the residue and the residue was again concentrated to dryness.

The residue was suspended in ethyl ether. The mixture was then stirred overnight, filtered and vacuum-dried at 30° C. for 15 hours. Eight g of a yellowish non-hygroscopic solid were obtained.

$$[\alpha]_D^{25} = -11.9 (c = 0.5\% \text{ DMF})$$

NMR DMSO δ 8.3 (2H, s, aromatic); 8.1 (2H, d, aromatic); 7.7 (2H, d, aromatic); 7.3–7.0 (4H, dm, aromatic); 5.4(2H, m, 2CH—OH); 4.6 (2H, s, $CH_2$-aromatic); 3.8–3.2(4H, dd, $2N^+CH_2$); 3.0(18H, s, $2(CH_3)_3N^+$); 2.6 (4H, m, $2\underline{CH}_2COO$); 2.4 (4H, m, 2 $\underline{CH}_2CH_3$); 1.0 (6H, m, $2CH_3$)

E.A. $C_{43}H_{34}N_2O_{14}$

|  | C% | H% | N% |
|---|---|---|---|
| Calculated | 62.3 | 7.1 | 3.4 |
| Found | 59.6 | 6.8 | 3.1 |

HPLC column: SGE-SAX (5 μm); 4.0×250 mm, T=30° C.

eluent: $CH_3CN/NH_4H_2PO_4$ 50 mM (72/78)

flow rate: 0.75 ml/min

Pamoic acid Rt 5.3 min, 42.5%

Propionyl L-carnitine Rt 9.43 min, 46.5

EXAMPLE 2

Preparation of Propionyl L-carnitine Acid Pamoate (ST 1341)

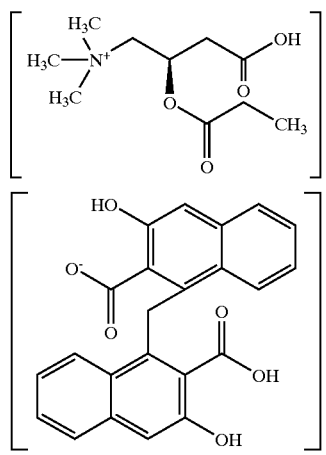

The compound was prepared as described in Example 1 with propionyl L-carnitine and pamoic acid in an equimolar ratio, $$[\alpha]_D^{25} = -10 (c = 1\% \text{ DMF})$$

M.P. 160° C. dec.

E.A. $C_{33}H_{29}NO_{10}$

|  | C% | H% | N% |
|---|---|---|---|
| Calculated | 66.1 | 4.9 | 2.3 |
| Found | 66.3 | 5.4 | 1.9 |

NMR DMSO δ 8.3 (2H, s, aromatic); 8.1 (2H, d, aromatic); 7.7 (2H, d, aromatic); 7.3 (2H, m, aromatic); 7.0 (2H, m, aromatic); 5.4 (1H, m, CHO); 4.6 (2H, s, $CH_2$-aromatic); 3.8–3.5 (2H, m, $N^+CH_2$); 3.0 (9H, s, $(CH_3)_3N^+$); 2.6 (2H, d, $CH_2COO$), 2.3 (1H, t, $\underline{CH_2}CH_3$); 0.9 (3H, t, $CH_3$)

HPLC

As described in Example 1

Pamoic acid 68.8%

Propionyl L-carnitine 24.2

EXAMPLE 3

Preparation of Acetyl L-carnitine Pamoate (ST 1335)

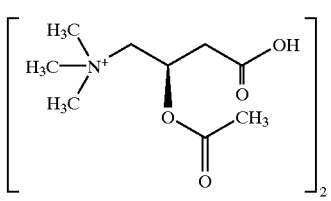

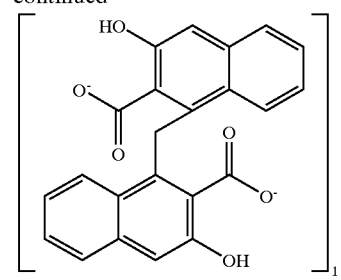

Acetyl L-carnitine inner salt (8.12 g; 0.04 mol) and pamoic acid (7.76 g; 0.02 mol) were suspended in 500 ml of acetone and 500 ml of $H_2O$. The mixture was stirred for 18 hours at ambient temperature until completely dissolved.

The yellow solution thus obtained was vacuum-concentrated to eliminate the acetone and the residual turbid aqueous solution was lyophilised.

14.3 g of solid non-hygroscopic product were obtained.

$$[\alpha]_D^{25} = -13.5 (c = 1\% \text{ DMF})$$

M.P. 160–170° C. dec.

E.A. $C_{41}H_{50}N_2O_4$

|  | C% | H% | N% |
|---|---|---|---|
| Calculated | 61.9 | 6.3 | 3.5 |
| Found | 59.5 | 6.4 | 3.2 |

$H_2O$ 4.5%

NMR DMSO δ 8.4 (4H, d-s, aromatic); 7.7 (2H, d, aromatic); 7.2–7.0 (4H, dm, aromatic); 5.5 (2H, m, 2CH—O); 4.7 (2H, m,$CH_2$-aromatic); 3.9–3.4 (4H, m,$2N^+CH_2$); 3.2 (18H, s, 2 $(CH_3)_3N^+$); 2.7 (4H, d, $2CH_2COO$); 2.1 (6H, s, $2CH_3$)

HPLC

As described in Example 1

Pamoic acid Rt 5.63 min, 45.3%

Propionyl L-carnitine Rt 11.21 min, 44.6%

EXAMPLE 4

Preparation of Acetyl L-carnitine Acid Pamoate (ST 1336)

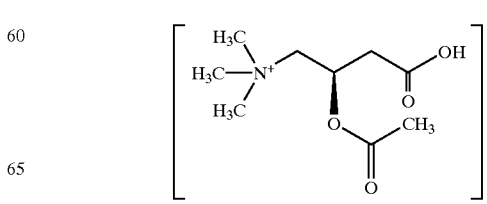

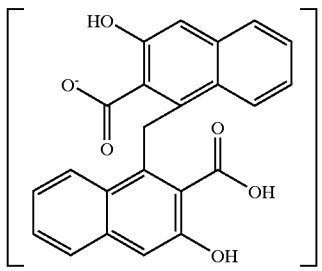

The compound was prepared as described in Example 3 with acetyl L-carnitine and pamoic acid in an equimolar ratio, $$[\alpha]_D^{25} = -4.9 (c = 1\% \text{ DMF})$$

M.P. 160° C. dec.
E.A. $C_{32}H_{33}NO_{10}$

|  | C% | H% | N% |
| --- | --- | --- | --- |
| Calculated | 64.9 | 5.6 | 2.4 |
| Found | 63.8 | 5.7 | 2.2 |

$H_2O$: 3.7%

NMR DMSO δ 8.4 (2H, s, aromatic); 8.2 (2H, d, aromatic); 7.8 (2H, d, aromatic); 7.4–7.1 (4H, dm, aromatic); 5.5 (1H, dm, CHO); 4.8 (2H, s,$CH_2$-aromatic); 3.9–3.6 (2H, m, $N^+CH_2$); 3.1 (9H, s, $(CH_3)_3N^+$); 2.7 (2H, d, $CH_2COO$), 2.1 (3H, d, $CH_3$)

HPLC
As described in Example 3
Pamoic acid 68.8%
Acetyl L-carnitine i.s. 27.4%

All compounds in Examples 1–4 proved to be non-hygroscopic and highly stable.

The invention described herein also comprises compositions containing as their active ingredient one of the above-mentioned non-hygroscopic salts and possibly one or more pharmacologically acceptable excipients well known to experts in pharmacy and food processing.

There is a particular preference for compositions in solid form suitable for the preparation of oral administration forms such as tablets, chewable tablets, capsules, granulates or powders comprising a L-carnitine or alkanoyl L-carnitine salt of formula (a) corresponding to 50-2000, and -preferably 100-1000 mg of L-carnitine or alkanoyl L-carnitine expressed as inner salt.

For example, the following is a composition suitable for the production of tablets:

| | |
| --- | --- |
| L-carnitine non-hygroscopic salt according to the invention | 500 mg |
| Starch | 20 mg |
| Talc | 10 mg |
| Calcium stearate | 1 mg |
| | 531 mg |

The following is a composition suitable for the production of capsules:

| | |
| --- | --- |
| L-carnitine non-hygroscopic salt according to the invention | 500 mg |
| Lactose | 50 mg |
| Starch | 20 mg |
| Talc | 5 mg |
| Calcium stearate | 2 mg |
| | 577 mg |

What is claimed is:

1. A non-hygroscopic salt consisting of L-carnitine or alkanoyl L-carnitine with pamoic acid of formula (I):

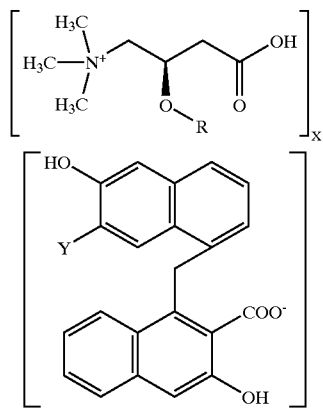

where R is hydrogen or a lower, linear or branched alkanoyl having 2–6 carbon atoms and where if X=1, Y=COOH and if X=2, Y=$COO^-$.

2. A salt according to claim 1, in which R is selected from the group consisting of acetyl, propionyl, butyryl, valeryl and isovaleryl.

3. A composition containing an excipient and as its active ingredient a salt according to claim 1.

4. A composition according to claim 3 wherein the excipient is a pharmacologically acceptable excipient.

5. A composition according to claim 3 in the form of a tablet, chewable tablet, capsule, granulate or powder.

6. A composition according to claim 3 in the form of a unit dose comprising a L-carnitine or alkanoyl L-carnitine salt of formula (I) as its active ingredient containing 50–2000 mg of L-carnitine or alkanoyl L-carnitine expressed as inner salt.

7. A composition of claim 6 containing as its active ingredient 100 to 1,000 mg g L-carnitine or alkanoyl L-carnitine.

8. A food supplement, dietetic product or pharmaceutical product of the composition of claim 4.

9. A veterinary food supplement comprising the composition of claim 4.

* * * * *